United States Patent [19]

Holst et al.

[11] 3,936,441

[45] Feb. 3, 1976

[54] PROCESS FOR THE PRODUCTION OF WATER ADSORBING BUT WATER-INSOLUBLE CELLULOSE ETHERS

[75] Inventors: Arno Holst, Wiesbaden-Biebrich; Michael Kostrzewa, Wiesbaden; Helmut Lask, Wiesbaden-Schierstein, all of Germany

[73] Assignee: Hoechst Aktiengesellschaft, Germany

[22] Filed: Nov. 11, 1974

[21] Appl. No.: 522,741

[30] Foreign Application Priority Data

Nov. 15, 1973 Germany............................ 2357079

[52] U.S. Cl. ..... 260/231 A; 260/17 A; 260/231 CM
[51] Int. Cl.² ................... C08B 11/00; C08B 11/20; C08B 11/193; C08B 15/10
[58] Field of Search ........ 260/231 A, 231 CM, 232, 260/17 A

[56] References Cited

UNITED STATES PATENTS

| | | | |
|---|---|---|---|
| 2,517,577 | 8/1950 | Klug et al. .................. | 260/231 CM |
| 2,886,474 | 5/1959 | Kine et al. .................. | 260/17 A |
| 3,029,232 | 4/1962 | Bikales et al. ............... | 260/231 A |
| 3,102,773 | 9/1963 | Needleman ................... | 260/231 A |
| 3,125,406 | 3/1964 | Herman ....................... | 260/17 A |
| 3,298,979 | 1/1967 | Hagemeyer et al............. | 260/17 A |
| 3,423,163 | 1/1969 | Magat et al. ................. | 260/17 A |

FOREIGN PATENTS OR APPLICATIONS

| | | | |
|---|---|---|---|
| 1,099,239 | 1/1968 | United Kingdom............... | 260/17 A |
| 45-40556 | 12/1970 | Japan......................... | 260/17 A |

*Primary Examiner*—Ronald W. Griffin
*Attorney, Agent, or Firm*—James E. Bryan

[57] ABSTRACT

This invention relates to an improvement in the process for the production of water-adsorbing, but largely water-insoluble, cellulose ethers, in which cellulose is alkalized in the presence of alkali hydroxide and isopropanol as a reaction medium and is so reacted with an etherification agent that by etherification only a water-soluble cellulose ether is produced, and in which process the cellulose is reacted with a crosslinking agent which is polyfunctional towards cellulose in an alkaline reaction medium before, during, or after the etherification of the cellulose, the improvement comprising effecting the etherification of cellulose to carboxymethyl cellulose, carboxymethyl hydroxyethyl cellulose, hydroxyethyl cellulose, or methylhydroxyethyl cellulose, reacting the cellulose with the polyfunctional cross-linking agent in the presence of 0.8 to 7.5 parts by weight of isopropanol, based upon the cellulose weight, and employing as the cross-linking agent acrylamido methylene chloroacetamide, dichloroacetic acid or phosphorus oxychloride or a compound in which at least two groups functional towards cellulose are the acrylic amino group

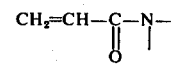

the chlorine azomethine group

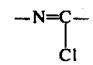

or the allyloxy azomethine group

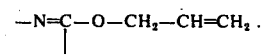

11 Claims, No Drawings

PROCESS FOR THE PRODUCTION OF WATER ADSORBING BUT WATER-INSOLUBLE CELLULOSE ETHERS

This invention relates to a process for the production of water-adsorbing, but largely water-insoluble, cellulose ethers.

It is known to cross-link water-soluble carboxymethyl cellulose, which can be produced by etherification of cellulose with monochloroacetic acid, in order to obtain a cellulose ether which is, at least partially, water-insoluble, but which has the capacity of adsorbing relatively large quantities of water, and of simultaneously swelling. The cross-linking may take place before, after, or simultaneously with, the etherification. Reaction agents which are polyfunctional towards cellulose are used as cross-linking agents, for example epoxy compounds, polychlorinated higher alcohols, or divinyl sulfone. Epichlorohydrin is preferably used, because the cross-linking with it can be carried out simultaneously with the etherification. The cross-linkings take place in the presence of water either in a semidry state or in the presence of relatively large quantities of an inert organic diluent, such as isopropanol, the quantity of which corresponds to a 40-fold quantity of cellulose. At standard temperature, the cross-linking reaction requires many hours, e.g. 18 hours; at a higher temperature the reaction is more rapid, but even at temperatures over 70°C several hours are required, e.g. 3.5 hours.

The object of the present invention is to provide a process for the production of water-adsorbing, but largely water-insoluble, i.e. more than fifty per cent by weight insoluble, cellulose ethers, which process can be carried out more rapidly. This object is obtained by proceeding from the known process for the production of water-adsorbing, but water-insoluble, cellulose ethers, in which process cellulose is reacted with an etherification agent in the presence of alkali and isopropanol as a reaction medium in such a way that, by means of a mere etherification, a largely, i.e. at least 95 percent by weight, water-soluble cellulose ether is produced and in which known process a reaction takes place before, simultaneously with, or after the etherification, with a cross-linking agent which is polyfunctional towards cellulose in an alkaline reaction medium. In the process according to the invention the etherification of cellulose is effected to carboxymethyl cellulose, carboxymethyl hydroxyethyl cellulose, hydroxyethyl cellulose, or methyl hydroxyethyl cellulose, the polyfunctional reaction medium is reacted with the cellulose in the presence of 0.8 to 7.5 parts by weight of isopropanol, in relation to the cellulose weight, and a cross-linking agent is employed, which is dichloroacetic acid or phosphorus oxychloride or a compound in which the groups functional towards cellulose are
the acrylic amino group

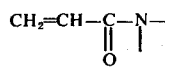

the chlorine azomethine group

or
the allyloxy azomethine group

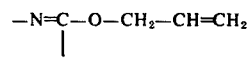

When applying the process to the production of carboxymethyl cellulose or carboxymethyl hydroxyethyl cellulose, the alkalization and etherification as well as the cross-linking are preferably carried out in the presence of 0.85 to 3.0 parts by weight of isopropyl alcohol per 1 part by weight of dry cellulose. When the process is applied to the production of hydroxyethyl cellulose or methyl hydroxyethyl cellulose, the alkalization, etherification and cross-linking are preferably carried out in the presence of at least 0.85 part by weight, but not more than 7 parts by weight of isopropyl alcohol. In the process it is often most advantageous to use isopropyl alcohol, hereinafter also called isopropanol, in the form of the water-containing product with about 13 percent by weight of water which is often used for technical purposes. In the present description, however, isopropyl alcohol or isopropanol are meant to be isopropyl alcohol of 100 per cent concentration, if no other explanation is given.

In order to provide the presence of alkali necessary for the process, aqueous lyes are used in most cases. During the alkalization, etherification, and cross-linking, the reaction mixture therefore contains, apart from the water introduced by the use of 87 percent isopropanol, water introduced by the alkali liquor employed. In some cases more water is introduced into the reaction mixtures by the fact that the cross-linking agent is added in the form of an aqueous solution. The entire quantity by weight of water introduced into the reaction mixture, however, should not exceed the quantity by weight of isopropanol present in the mixture. It preferably should be less than two thirds of the quantity by weight of the isopropanol.

If, in the production of carboxymethyl cellulose or carboxymethyl hydroxyethyl cellulose, the etherification is carried out before the cross-linking, and if this is done in the presence of a substantially higher amount of isopropanol than 3 parts by weight per 1 part by weight of cellulose, it is advisable to remove some of the isopropanol before the cross-linking of the cellulose ether, so that it takes place in the presence of about 3 parts by weight of isopropanol. Otherwise the cross-linking is less rapid, if the same quantity of cross-linking agent is used.

The cross-linking agents used in the process are, for example:
methylene-bis-acrylamide
N-N'-dimethylol methylene bisacrylamide
trisacrylol hexahydro triazine
acrylamido methylene chloroacetamide
2,4,6-trichloropyrimidine
2,4,5,6-tetrachloropyrimidine
cyanuric chloride
triallyl cyanurate
dichloroacetic acid
phosphorus oxychloride Depending upon the type of the cross-linking agent, 0.001 to 0.20 part by weight per 1 part by weight of cellulose are preferably applied. An exception is the cross-linking agent dichloroacetic acid. More than 0.10 part by weight thereof per part by weight of cellulose must be used. If monochloroacetic acid is used alone or together with ethylene oxide as an etherification agent, the amount of dichloroacetic acid must be relatively high compared with the quantity of monochloroacetic acid employed. The quantity ratio to be employed depends upon the quantity of isopropanol which is present during the process of cross-linking. The more isopropanol present, the higher the quantity of dichloroacetic acid must be. If salts of monochloroacetic acid or dichloroacetic acid are used, their quantities must be recalculated corresponding to the free acids. The process leads, as do the previously known corresponding processes, to cross-linked products which contain a certain water-soluble portion. For many purposes this does not matter, so that a removal of the water-soluble portion is in most cases unnecessary. The table below gives the percentages by weight of the cross-linked cellulose ethers mentioned in the examples which are soluble in pure water at 20°C.

The process requires relatively small quantities of a reaction medium (isopropanol) and, at temperatures of about 78°C, it very rapidly leads to sufficient cross-linkings, i.e. in about one hour. Products are obtained which have, depending upon the conditions of etherification and cross-linking, different capacities for adsorbing water. Therefore, many different requirements can be met. The capacity of adsorbing water can be extremely high, for example up to an 80-fold weight of the cross-linked cellulose ether. The adsorbed water is so firmly bonded to the product of the cross-linking that even a centrifugal force corresponding to a 2,000-fold acceleration of gravity cannot remove it. The table below shows the retention capacity towards pure water at 20°C after the application of such a centrifugal force.

The cross-linked cellulose ethers obtained according to the process may serve various technical purposes, for example as adsorbing materials for medical and hygienic bandages or as dehydrating agents, e.g. for aqueous emulsions.

In the following examples all percentages are percent by weight. The alkalization, etherification, and cross-linking are carried out at the given temperatures, during kneading and stirring (depending upon the quantity of isopropanol-water reaction medium which is present). The products obtained are, if nothing else is stated, neutralized, washed, and then dried, as described in Example 1.

EXAMPLE 1

20 kg of cellulose in 60 kg of 87 percent aqueous isopropanol are alkalized with 9.2 kg of soda lye (50 percent) by intensive mixing for 45 minutes at 20°C. Then the alkali cellulose thus produced is cross-linked by adding 2.2 kg of an aqueous 30 percent solution of dimethylol methylene bis-acrylamide and is reacted for one hour at 50°C, while the kneading is continued. Then, the mixture is etherified by adding 11 kg of the sodium salt of monochloroacetic acid and by kneading it for one hour at 70°C. Then it is neutralized with acetic acid, washed salt-free with 80 percent methanol, and dried.

The water retention capacity of the cross-linked cellulose ether obtained, expressed in grams of water per 100 g of cellulose ether, as well as its water-soluble content in percent by weight, are given in the table following the examples. It also gives the corresponding data for the following examples.

EXAMPLE 2

100 g of cellulose in 300 g of 87 per cent isopropanol are alkalized with 65 g of soda lye (50 percent) by kneading them for 45 minutes at 20°C. Then the mixture is etherified by adding 82 g of the sodium salt of monochloroacetic acid and by kneading it for another hour at 70°C. Then it is cross-linked with 50 g of dimethylol methylene bisacrylamide (30 per cent) while it is kneaded for one hour at 50°C.

EXAMPLE 3

100 g of cellulose are suspended in 850 ml of 87 per cent isopropanol while 65 g of soda lye (50 percent) are added, and then the mixture is alkalized for 45 minutes at 20°C while it is stirred. Then it is etherified by adding 82 g of the sodium salt of monochloroacetic acid within one hour at 70°C, without stopping the stirring. After the etherification, the muddy reaction material is pressed off to an extent such that the weight of the carboxymethyl cellulose ether is about 400 g. Then, 50 g of dimethylol methylene bisacrylamide (30 per cent) are added and the mixture is cross-linked by kneading it for 1 hour at 50°C.

EXAMPLE 4

20 kg of cellulose are alkalized in 170 l of isopropanol (87 percent) while 44 kg of 13.64 percent soda lye are added and the mixture is intensively stirred in a pressure vessel for one half hour at 20°C. The mixture is then mixed with 13 kg of ethylene oxide. Etherification is carried out for one hour at 70°C. After adding 1 kg of a 30 percent aqueous solution of dimethylol methylene bisacrylamide, the temperature is maintained at 50°C for one hour. Then the mixture is neutralized, washed out with a methanol-acetone mixture (1 : 1), and dried.

EXAMPLE 5

100 g of cellulose are alkalized with 170 g of soda lye (38.2 percent) in 300 g of 87 per cent isopropanol for one hour at 20°C. Then 50 g of a 30 per cent aqueous solution of dimethylol methylene bisacrylamide are added. Cross-linking is carried out for one hour at 50°C. The cross-linked alkali cellulose obtained is etherified in an autoclave with 25 ml of ethylene oxide and 800 ml of methyl chloride within one hour at 85°C.

EXAMPLE 6

100 g of cellulose in 300 g of isopropanol (87 percent) are alkalized with 64 g of soda lye (50 percent) for 45 minutes at 20°C. After adding 55 g of the sodium salt of monochloroacetic acid, the mixture is etherified for one hour at 80°C. Then 1.1 g of glacial acetic acid mixed with 50 ml of isopropanol are sprayed onto the mixture in order to largely neutralize the soda lye and thus to stop the decomposition of the cellulose. Then the mixture is homogenized by kneading it. Then 15 g of methylene bisacrylamide, dissolved in 35 g of water, are added. The cellulose ether treated in this manner is stored for 60 hours at standard temperature and then treated as in the above Example 1. The relatively long cross-linking time is due to the very low content of soda lye and the low temperature.

EXAMPLE 7

100 g of cellulose in 300 g of isopropanol (87 per cent) are alkalized with 56 g of soda lye (50 per cent) for 45 minutes at 20°C. After adding 15 g of methylene bisacrylamide (dissolved in 35 g of water) the mixture is cross-linked for one hour at 50°C while it is kneaded. Then it is etherified with 24.8 g of monochloroacetic acid for one hour at 70°C. Then a further etherification takes place in an autoclave for one hour at 70°C, while 38 ml of ethylene oxide are added.

EXAMPLE 8

100 g of cellulose in 300 g of isopropanol (87 per cent) are alkalized with 46 g of soda lye (50 percent). After adding 10 g of 2,4,6-trichloropyrimidine, dissolved in 50 ml of isopropanol (87 per cent), the cross-linking is carried out within one hour at 80°C. Then 55 g of the sodium salt of monochloroacetic acid are added and the mixture is etherified for one hour at 80°C.

EXAMPLE 9

The process is the same as in Example 8, except that instead of 2,4,6-trichloropyrimidine, 10 g of 2,4,5,6-tetrachloropyrimidine are added.

EXAMPLE 10

300 g of cellulose in 900 g of isopropanol (87 percent) are alkalized with 203 g of 48 percent soda lye for one half hour at standard temperature. Then 246 g of the sodium salt of monochloroacetic acid are added, and the etherification is carried out for one hour at 70°C. 4.5 g of cyanuric chloride, dissolved in 50 ml of acetone, are added dropwise to this raw carboxymethyl cellulose, and cross-linking is carried out for one hour at 70°C. After the neutralization with acetic acid, the mixture is washed salt-free with 90 percent methanol, and dried.

EXAMPLE 11

20 kg of cellulose in 60 kg of isopropanol (87 percent) are alkalized with 12.8 kg of soda lye (49.5 percent) for 45 minutes at standard temperature in a pressure vessel, during intensive mixing. Then a mixture of 10.8 kg of the sodium salt of monochloroacetic acid and 2.25 kg of dichloroacetic acid is added. Then, the mixture is etherified for one hour at 85°C. Then the mixture is neutralized, washed salt-free, and dried.

EXAMPLE 12

100 g of cellulose in 300 g of isopropanol (87 percent) are alkalized with 77 g of soda lye (50 per cent) for 45 minutes at 20°C. Then 33.8 g of dichloroacetic acid, which are dissolved in 43 ml of isopropanol (100 percent), and 37 ml of ethylene oxide are added, and the etherification is carried out for one hour at 80°C. Then the mixture is neutralized, washed salt-free, and dried.

EXAMPLE 13

100 g of cellulose in 670 g of isopropanol (100 percent) are alkalized with 30 g of NaOH, dissolved in 189 g of water, for one half hour at 20°C. After 119 ml of ethylene oxide are added, the mixture is etherified for one hour at 70°C. Then 11.5 g of cyanuric chloride in the form of powder are added, and cross-linking is carried out for one hour at 70°C. The product is neutralized, washed saltfree, and dried.

EXAMPLE 14

100 g of cellulose are alkalized with 130 g of soda lye (50 percent) in 300 g of 87 percent isopropanol for one hour at 20°C. The alkali cellulose thus obtained is etherified in a stirring autoclave with 25 ml of ethylene oxide and 800 ml of methyl chloride within one hour at 85°C. Then a solution of 0.58 g of cyanuric chloride in 30 g of isopropanol is added dropwise and cross-linking is carried out by maintaining the mixture at boiling temperature for one hour while the stirring is continued. The product obtained is neutralized as described in Example 1, washed salt-free, and dried.

EXAMPLE 15

100 g of cellulose in 670 g of isopropanol are alkalized with 30 g of NaOH, dissolved in 189 g of water, for one hour at 20°C. Then 119 ml of ethylene oxide are added and etherification is carried out by leaving the mixture standing for one hour at 70°C. Then 48 g of the sodium salt of dichloroacetic acid are added to the pulp thus obtained, and the temperature is then maintained at 80°C for one hour. After the neutralization, the mixture is washed salt-free and dried.

EXAMPLE 16

100 g of cellulose in 670 g of isopropanol (100 percent) are alkalized with 30 g of NaOH, which are dissolved in 189 g of water, for one half hour at 20°C. Then 14.7 g of methylene bisacrylamide, dissolved in 50 ml of isopropanol, are added. Cross-linking is carried out for one hour at 50°C. Then the etherification takes place with 75 ml of ethylene oxide at 70°C within one hour. Then the mixture is neutralized, washed out, and dried.

EXAMPLE 17

100 g of cellulose are alkalized with 65 g of NaOH, which are dissolved in 105 g of water, for one hour at 20°C. Then 14.7 g of methylene bisacrylamide, dissolved in 50 ml of isopropanol, are added. Cross-linking is carried out for one hour at 50°C. The reaction mixture thus obtained is reacted with 25 ml of ethylene oxide and 800 ml of methyl chloride and then etherified for one hour at 85°C. Then it is washed salt-free and dried.

EXAMPLE 18

100 g of cellulose are alkalized with 46 g of soda lye (50 percent) in 300 g of isopropanol (87 percent) for 45 minutes at 20°C. Then 10.2 g of acrylamidomethylene chloroacetamide, dispersed in 50 ml of isopropanol, are added, and the mixture is cross-linked for one hour at 50°C. Then 55 g of the sodium salt of monochloroacetic acid are added and etherification is carried out within one hour at 70°C. Then the product is washed salt-free and dried.

EXAMPLE 19

100 g of cellulose are alkalized with 46 g of soda lye (50 percent) in 300 g of isopropanol (87 per cent) for 45 minutes at 20°C. Then 55 g of the sodium salt of monochloroacetic acid are added and etherification is carried out within one hour at 70°C. Then the mixture is reacted with 12.8 g of trisacryloyl hexahydrotriazine dissolved in 50 ml of isopropanol (87 per cent), and cross-linking is carried out therewith by kneading the mixture for one hour at 50°C. After neutralization, it is washed salt-free and dried.

EXAMPLE 20

Non-cross-linked hydroxyethyl cellulose is produced as described in Example 13, but then 100 g of the hydroxyethyl cellulose are cross-linked with 1.36 g of triallyl cyanurate which is dissolved in 60 ml of isopropanol.

EXAMPLE 21

Non-cross-linked hydroxyethyl cellulose is produced as described in Example 13, but 100 g of the hydroxyethyl cellulose are cross-linked with 0.3 g of phosphorus oxychloride, which is dissolved in 20 ml of isopropanol (100 percent). The phosphorus oxychloride solution is added to the reaction material after the material has cooled to 20°C. Then this temperature is maintained constant for one hour for the cross-linking.

EXAMPLE 22

100 g of cellulose are alkalized with 46 g of 50 percent soda lye in 100 g of 87 per cent isopropanol by kneading it for 45 minutes at 20°C. Then the reaction material is kneaded with 55 g of the sodium salt of monochloroacetic acid, the temperature is raised to 70°C, and the kneading is continued for one hour. Then the mixture is reacted with 50 g of a 30 percent aqueous solution of N,N'-dimethylol methylene bisacrylamide, and the kneading is continued for another hour at 50°C. Then the product obtained is neutralized, washed, and dried.

EXAMPLE 23

100 g of cellulose in 800 g of 87 percent isopropanol are alkalized with 250 g of 20 percent soda lye in a stirring autoclave while being kneaded for 30 minutes at 20°C. Then 31 g of methyl chloride and 109 g of ethylene oxide are added, the temperature is raised to 70°C and maintained constant until the pressure falls, i.e. for one hour, while the kneading is continued. Then 50 g of a 30 percent aqueous solution of dimethylol methylene bisacrylamide are added and the kneading is continued for another hour, while the temperature is maintained at about 50°C. The product obtained is neutralized, washed, and dried.

| Example No. | Capacity of retaining water in g of water per 100 g of cellulose ether. | Water-soluble portion, in percent by weight. |
|---|---|---|
| 1 | 2,880 | 21.0 |
| 2 | 4,920 | 39.2 |
| 3 | 8,740 | 42.7 |
| 4 | 2,070 | 20.1 |
| 5 | 2,460 | 35.2 |
| 6 | 3,310 | 22.6 |
| 7 | 940 | 14.4 |
| 8 | 5,100 | 30.9 |
| 9 | 5,920 | 34.8 |
| 10 | 600 | 30.0 |
| 11 | 2,200 | 15.5 |
| 12 | 560 | 13.5 |
| 13 | 700 | 7.0 |
| 14 | 2,200 | 48.0 |
| 15 | 575 | 46.6 |
| 16 | 3,400 | 34.9 |
| 17 | 3,150 | 28.8 |
| 18 | 3,430 | 24.5 |
| 19 | 650 | 27.2 |
| 20 | 410 | 14.0 |
| 21 | 420 | 16.4 |
| 22 | 2,150 | 28.0 |
| 23 | 2,970 | 22.0 |

It will be obvious to those skilled in the art that many modifications may be made within the scope of the present invention without departing from the spirit thereof, and the invention includes all such modifications.

What is claimed is:

1. In the process for the production of water-adsorbing, but largely waterinsoluble, cellulose ethers, in which cellulose is alkalized in the presence of alkali hydroxide and isopropanol as a reaction medium and is so reacted with an etherification agent that by etherification only a water-soluble cellulose ether is produced, and in which process the cellulose is reacted with a cross-linking agent which is polyfunctional towards cellulose in an alkaline reaction medium before, during, or after the etherification of the cellulose, the improvement which comprises effecting the etherification of cellulose to carboxymethyl cellulose, carboxymethyl hydroxyethyl cellulose, hydroxyethyl cellulose, or methylhydroxyethyl cellulose, reacting the cellulose with the polyfunctional cross-linking agent in the presence of 0.8 to 7.5 parts by weight of isopropanol, based upon the cellulose weight, and employing as the cross-linking agent acrylamido methylene chloroacetamide, dichloroacetic acid or phosphorus oxychloride or a compound in which at least two groups functional towards cellulose are the acrylic amino group

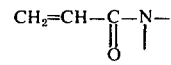

the chlorine azomethine group

or the allyloxy azomethine group

2. A process according to claim 1 in which the croslinking agent is dimethylol methylene bisacrylamide.

3. A process according to claim 1 in which the cross-linking agent is methylene bisacrylamide.

4. A process according to claim 1 in which the cross-linking agent is 2,4,6-trichloropyrimidine.

5. A process according to claim 1 in which the cross-linking agent is 2,4,5,6-tetrachloropyrimidine.

6. A process according to claim 1 in which the cross-linking agent is cyanuric chloride.

7. A process according to claim 1 in which the cross-linking agent is acrylamidomethylene chloroacetamide.

8. A process according to claim 1 in which the cross-linking agent is trisacrylol hexahydrotriazine.

9. A process according to claim 1 in which the cross-linking agent is triallyl cyanurate.

10. A process according to claim 1 in which the cross-linking agent is phosphorus oxychloride.

11. A process for the production of water-adsorbing, but largely water-insoluble cellulose ethers which comprises alkalizing cellulose in the presence of alkali hydroxide and 0.8 to 7.5 parts by weight of isopropanol as a reaction medium, based upon the cellulose weight, reacting the alkalized cellulose with an etherification agent so that by etherification only a water-soluble carboxymethyl cellulose, carboxymethyl hydroxyethyl cellulose, hydroxyethyl cellulose, or methylhydroxyethyl cellulose is produced, and reacting said cellulose, before, during, or after the etherification thereof with a cross-linking agent selected from the group consisting of methylene bisacrylamide, N-N'-dimethylol methylene bisacrylamide, trisacrylol hexahydro triazine, acrylamido methylene chloroacetamide, 2,4,6-trichloropyrimidine, cyanuric chloride, triallyl cyanurate, dichloroacetic acid, and phosphorus oxychloride, whereby a cross-linked cellulose ether is obtained which is more than 50 percent by weight water-insoluble.

* * * * *